United States Patent [19]

Huynh-Ba et al.

[11] Patent Number: 5,120,467
[45] Date of Patent: Jun. 9, 1992

[54] ANISOTROPIC COMPOUNDS AND LIQUID CRYSTAL MIXTURES

[75] Inventors: Tuong Huynh-Ba, Pully; Maged A. Osman, Zürich, both of Switzerland

[73] Assignee: Merck Patent Gesellschaft mit beschrankter Haftung, Darmstadt, Fed. Rep. of Germany

[21] Appl. No.: 333,769

[22] Filed: Apr. 6, 1989

Related U.S. Application Data

[60] Continuation-in-part of Ser. No. 917,138, Oct. 9, 1986, abandoned, which is a division of Ser. No. 648,431, Sep. 10, 1984, Pat. No. 4,723,005.

[30] Foreign Application Priority Data

Sep. 10, 1983 [DE] Fed. Rep. of Germany ....... 3332692

[51] Int. Cl.$^5$ .................. C09K 19/34; C09K 19/30
[52] U.S. Cl. .................. 252/299.61; 252/299.63; 252/299.5; 252/299.6
[58] Field of Search .............. 252/299.61, 299.63, 252/299.5, 299.6

[56] References Cited

U.S. PATENT DOCUMENTS

| | | | |
|---|---|---|---|
| 4,027,950 | 6/1977 | Moriyama et al. | 252/299.5 |
| 4,147,655 | 4/1979 | Dubois et al. | 252/299.67 |
| 4,191,776 | 3/1980 | Nickl et al. | 560/11 |
| 4,293,404 | 10/1981 | Deutscher et al. | 252/299.63 |
| 4,344,856 | 8/1982 | Demus et al. | 252/299.61 |
| 4,348,324 | 9/1982 | Demus et al. | 252/299.61 |
| 4,393,231 | 7/1983 | Misaki et al. | 252/299.67 |
| 4,550,981 | 11/1985 | Petrzilka et al. | 252/299.63 |
| 4,572,794 | 2/1986 | Eidenschink et al. | 252/299.63 |
| 4,576,732 | 3/1986 | Isogai et al. | 252/299.67 |
| 4,592,858 | 6/1986 | Higuchi et al. | 252/299.66 |
| 4,596,667 | 6/1986 | Inukai et al. | 252/299.67 |
| 4,613,209 | 9/1986 | Goodby et al. | 252/299.67 |
| 4,622,163 | 11/1986 | Huynh-Ba et al. | 252/299.63 |
| 4,657,695 | 4/1987 | Saito et al. | 252/299.61 |
| 4,668,427 | 5/1987 | Saito et al. | 252/299.6 |
| 4,694,098 | 9/1987 | Hirai et al. | 252/299.63 |
| 4,695,650 | 9/1987 | Walba et al. | 252/299.67 |
| 4,695,651 | 9/1987 | Higuchi et al. | 252/299.66 |
| 4,725,688 | 2/1988 | Taguchi et al. | 252/299.61 |

FOREIGN PATENT DOCUMENTS

| | | |
|---|---|---|
| 0159872 | 10/1985 | European Pat. Off. |
| 0174816 | 3/1986 | European Pat. Off. |
| 0191600 | 8/1986 | European Pat. Off. |
| 0225195 | 6/1987 | European Pat. Off. |
| 2010271 | 2/1970 | France |
| 1249492 | 10/1981 | United Kingdom |

OTHER PUBLICATIONS

Tsumo, Y. et al, Bull. Chem. Soc. Jpn., vol. 51(2), pp. 596-600 (1978).
Goodby, J. W. et al, Liquid Crystals and Ordered Fluids, vol. 4, Griffin, A., et al, Ed., Plenum Press, N.Y., pp. 1-32 (1974), Proceedings of an ACS symposium, Las Vegas, Mar. 29-Apr. 1, 1982.
Demus, D., Nonemissive Electrooptic Displays, pp. 83-119 (1975).
Dabrowski, R., et al, Mol. Cryst. Liq. Cryst., vol. 87, pp. 109-135 (1982).

Primary Examiner—Robert L. Stoll
Assistant Examiner—Cynthia Harris
Attorney, Agent, or Firm—Millen, White & Zelano

[57] ABSTRACT

New anisotropic compounds of the formula (1) are useful in liquid crystal mixtures for electrooptical displays; at least one of the end groups of the compounds (1) is an alkyl group which carries cyano or halogen in a terminal or non-terminal position. This offers advantages for longitudinal polarization and/or cross-polarization of the anisotropic compounds with the aid of the comparatively highly polarizing cyano or halogen substituents, in particular high clear points, low $$\frac{\Delta \epsilon}{\epsilon_\perp}$$

values and/or negative $\Delta \epsilon$ values.

26 Claims, No Drawings

ANISOTROPIC COMPOUNDS AND LIQUID CRYSTAL MIXTURES

CROSS-REFERENCE TO RELATED APPLICATION

This application is a continuation-in-part of application Ser. No. 06/917,138, filed Oct. 9, 1986, abandoned which is a divisional of Ser. No. 648,431, filed Sept. 10, 1984, U.S. Pat. No. 4,723,005.

The invention relates to new anisotropic compounds for use in liquid crystal mixtures (LC mixtures) for electrooptical displays. The invention also relates to LC mixtures containing the new anisotropic compounds.

As is known, anisotropic compounds, the molecules of which carry, for polarization in the direction of the longitudinal axis of the molecule and/or at right angles thereto, certain substituents which effect this polarization, are required for the operation of various types of electrooptical displays. The polarization effect thereby caused is manifested by the positive or negative anisotropy of the dielectric constant (DCA or $\Delta\epsilon$) measured parallel ($\epsilon''$) and perpendicularly ($\epsilon\bot$) to the molecular axis, where $\Delta\epsilon = \epsilon'' - \epsilon\bot$.

Virtually all the known anisotropic compounds for liquid crystal mixtures contain two to four cyclic radicals which are linked with one another by bridge members (covalent bonds or particular divalent groups), and in most cases also carry so-called end groups, according to the general formula I

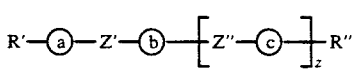

in which R' and R" are the end groups, a, b and c are the cyclic radicals and Z' and Z" are the bridge members; z is 0, 1 or 2.

In a typical case, polarization in the direction of the longitudinal axis of the molecule—called longitudinal polarization for short below—and accordingly the contribution to $\epsilon''$ is effected by a highly polarizing terminal group, such as the cyano group, on one end of the molecule (as R' or R") and an alkyl or alkoxy group on the other end of the molecule (R" or R').

The polarization at right angles to the longitudinal axis of the molecule—called cross-polarization for short below—is generally effected by polarizing substituents in the "lateral" position, and in particular hitherto virtually always by substituents on rings, such as cyano or halogen atoms, usually fluorine or chlorine, on the aromatic cyclic radicals, usually benzene rings, in accordance with the formula II

in which X' is the polarizing group, n is 1 or 2 and the arrows approximately correspond to the longitudinal axis of the molecule.

Formula II shows unambiguously that this customary type of cross-polarization with the aim of increasing $\epsilon\bot$, for example for anisotropic substances with an overall negative DCA or for anisotropic substances with a positive DCA and at the same time by use of the smallest possible values of the ratio $$\frac{\Delta\epsilon}{\epsilon\bot},$$

unavoidably leads to a considerable widening of the molecule, which is a disadvantage because it leads to a reduction in the clear point, and may result in other disadvantages. The limitation of the cross-polarization according to formula II to the presence of at least one aromatic ring in the molecule can also have an adverse effect.

The desirability of anisotropic compounds with a positive DCA and as small as possible values of $$\frac{\Delta\epsilon}{\epsilon\bot}$$

is illustrated, for example, in commonly assigned European Application No. 79,200,259.4, and is achieved there by combination of longitudinal polarization and cross-polarization with substituents on rings.

However, problems also result in longitudinal polarization without cross-polarization of the molecule if a highly polarizing substituent must be attached to a cycloaliphatic radical. As is known, the replacement of the aromatic rings by cycloaliphatic radicals often offers various advantages, such as lower viscosity and reduced optical anisotropy; however, it is found that substituents on the rings, such as cyano groups on cycloaliphatic radicals, lead to a reduction in the clear point or can even effect disappearance of the mesophase, especially if O or N is at the same time bonded directly to the cycloaliphatic radical. Thus, for example, cyclohexyl derivatives with a terminal nitrile group, according to formula III

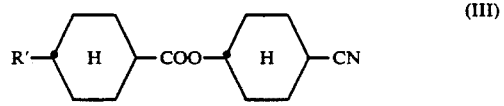

exhibit no mesophases, while the analogous phenylcyclohexyl derivatives of the formula IV

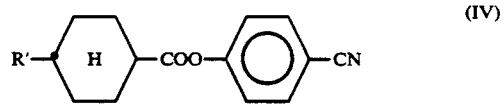

still have clear points between 70° and 80° C.

In the investigations leading to the present invention, it was found that the conformation energy of the groupings which form the anisotropic molecule, in particular the polarizing substituents, and the difference between the free conformation energy $-\Delta G_\chi^o$ of the groupings and substituents is of importance for their effect in reducing the clear point, and that it should be possible favorably to influence this effect by suitable choice of the substituents for longitudinal polarization and/or cross-polarization.

SUMMARY OF THE INVENTION

Thus, it is an object of this invention to provide new anisotropic compounds for LC mixtures for the operation of electrooptical displays, which enable the longitudinal polarization and/or cross-polarization problems mentioned to be solved or significantly ameliorated.

Upon further study of the application and appended claims, further objects and advantages of this invention will become apparent to those skilled in the art.

These objects have been achieved by introducing highly polarizing substituents chosen from the group comprising cyano and halogen, such as fluorine or chlorine, into the alkyl part of an end group of particular anisotropic molecules.

The invention relates to new anisotropic compounds of the formula (I)

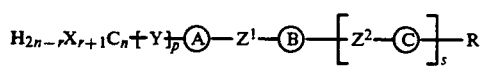

which is defined as follows: the rings A, B and C are identical or different and are chosen from the cycloaliphatic radicals of the formulae (1a) and (1b)

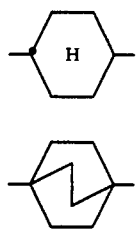

that is to say the trans-1,4-cyclohexyl and 1,4-bicyclo-(2,2,2)-octyl radicals, and aromatic radicals of the formulae (1c), (1d) and (1e)

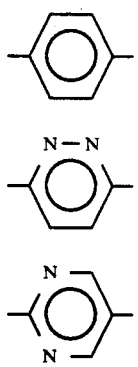

that is to say the 1,4-phenyl, 3,6-pyridazinyl and 2,5-pyrimidinyl radicals. The radical X, that is to say the highly polarizing group, at least one or more of which are present in the molecule, is the cyano group or a halogen atom, halogen atoms being fluorine and chlorine, in preference to bromine, and iodine being least preferred. At most one X may be attached to in each case one $C_n$ atom.

Y is an optional structural component (that is to say p is 0 or 1), and is the oxygen atom (—O—), the carboxyl group (—C(O)—O— or —O( O)C—) or the imino group (—N(H)—). If A is an aliphatic ring of the formula (1a) or (1b), p is preferably 0.

The bridges $Z^1$ and $Z^2$ can be identical or different and are covalent bonds or groups of the formula

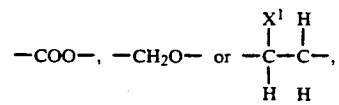

wherein $X^1$ is hydrogen or has one of the meanings given for X, and the groups can also be in the particular reverse sequence —OOC—, —OCH$_2$— and —CH$_2$C(X$^1$) (H)—, as long as these are not excluded by the provisos given below.

If $X^1$ has one of the meanings given for X, that is to say is cyano or halogen (F and Cl preferred as halogen), the corresponding bridge member contributes towards cross-polarization of the molecule of the formula (1). However, $X^1$ can only be one of the X groups if the end group R or $R^1$ is also one of the X groups.

The index n is a number from 1 to 12; in a preferred group of compounds of the formula (1), r is 0 or 1, but can also be greater with a corresponding chain length of the alkyl part; r is preferably 0.

The ring C is an optional component of compounds according to the invention, that is to say s like p is 0 or 1.

R can have one of the meanings given for $X^1$ if the adjacent ring C (if s=1) or B (if s=0) is an aromatic radical of the formula (1c), (1d) or (1e); in addition, R can be alkyl ($H_{2m+1}C_m$—), alkoxy ($H_{2m+1}C_m$—O—), alkoxycarbonyl ($H_{2m+1}C_m$—OC(O)—), alkylcarbonyloxy ($H_{2m+1}C_m$—C(O)—O—) or alkylamino ($H_{2m+1}C$—N(H)—) group, the alkyl part of which contains 1 to 12 C atoms (m=1-12) in a straight or branched, optionally chiral chain. Examples of the alkyl parts of the groups mentioned are methyl, ethyl, propyl, butyl, pentyl, hexyl, heptyl, octyl, nonyl, decyl, undecyl and dodecyl groups, including the isomeric and chiral-isomeric alkyl groups, such as 1-methylpropyl, 1-methylbutyl, 2-methylbutyl, 1-methyl-pentyl, 2-methylpentyl, 3-methylpentyl, 1- or 2- or 3- or 4-methylhexyl and 1- or 2- or 3-or 4- or 5-methylheptyl, as well as the other alkyl-alkyl groups with an asymmetric C atoms which are formed according to this principle.

The alkyl parts of R can carry one or more substituents, in particular halogen atoms or cyano groups, but at most in each case one such substituent is attached to in each case one C atom of the alkyl part. Furthermore, R can be a radical of the formula (1f)

in which the ring D independently is one of the rings given for A, B and C, $Z^3$ independently has one of the meanings given for $Z^1$ and $Z^2$ and $R^1$ has one of the meanings given for R, with the exception of the radical of the formula (1f).

According to the invention, the formula (1) is subject to the following restrictive provisos (a), (b), (c) and (d):

(a) no oxygen atom, on the one hand, and no oxygen or nitrogen atom or radical X, on the other hand, are at the same time bonded directly to any of the cycloaliphatic radicals of the formulae (1a) and (1b) present in the molecule of the formula (1); in other words, the molecule may not contain any rings of the formulae

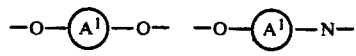

-continued and

−O−−X− wherein $A^1$ is a radical of the formula (1a) or (1b);
b) no groups of the formulae —CH$_2$O— and
—C(X) (H)— are bonded directly, with the C
atoms of this group, to any of the aromatic radicals
of the formulae (1c), (1d) and (1e) present in the
molecule of the formula (1), except when X is the
fluorine atom; in other words, the molecule may
not contain any rings of the formulae

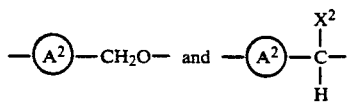

wherein $A^2$ is a radical of the formula (1c), (1d) or
(1e) and $X^2$ is cyano, chlorine, bromine or iodine,
but not fluorine;
c) the molecule of the formula (1) contains a total of
at least two radicals X if p, r and s are 0 and also $Z^1$
is the carboxyl group and the ring A is the radical
of the formula (1c), bonded to a group of the formula —CH$_2$CH$_2$CN; the second radical X here can
optionally be part of the left or right end group or
can be attached to a bridge member, and
d) $X^1$ can only be one of the meanings of X, that is to
say can be cyano or halogen, if R and/or $R^1$ also
have one of the meanings for X.

The provisos (a) and (b) result from the fact that
compounds of the formula (1) without these provisos do
not have clear points or have clear points which are too
low and/or do not have the required stability. The
provisos (c) and (d) serve for the purpose of delimitation.

DETAILED DISCUSSION

The knowledge, on which the invention is based, that
the introduction of polarizing substituents into end alkyl
groups offers a large number of new anisotropic compounds with low $$\frac{\Delta\epsilon}{\epsilon\perp}$$

values, irrespective of whether the rings of the molecule
are only cycloaliphatic radicals or only aromatic radicals, or whether cycloaliphatic radicals are combined
with aromatic radicals, is new and surprising. In this
case, the molecule of the new compounds (1) according
to the invention contains a combination of longitudinally polarizing X and cross-polarizing X, for example a
terminal X at the end of an end group or directly on an
aromatic ring, together with at least one lateral X as
part of an end group.

The knowledge on which the invention is based furthermore offers a large number of new, highly longitudinally polarizing anisotropic compounds, in which the
longitudinally polarizing cyano or halogen atom is terminal on an alkyl radical of an end group attached to a
cycloaliphatic radical; longitudinally polarizing compounds with high clear points are thereby obtainable.

This longitudinal polarization by cyano or halogen in
the end group of a cycloaliphatic radical can optionally
be combined with cross-polarizing cyano or halogen in
an end group or/and a bridge member.

If the compound (1) according to the invention is to
have a markedly positive DCA, it will in most cases
carry an end group which contains or consists of a
terminal X—preferably cyano. It should be taken into
consideration here, as also in the overall polarization
variations described below, that a non-terminal X in the
end groups can also contribute towards longitudinal
polarization.

If the compound (1) is to have as small as possible a
value of $$\frac{\Delta\epsilon}{\epsilon\perp}$$

with a more or less markedly positive DCA, it carries
an end group which contains a terminal X, preferably
cyano, or consists of such a group, combined with at
least one non-terminal X in an end group and/or an X
on a bridge.

Compounds (1) with negative DCA are obtained
when the sum of the lateral polarization contributions of
X in the end groups and/or bridges exceeds the sum of
the longitudinally polarizing contributions, or if the
longitudinally polarizing groups are absent.

Preferred groups of compounds of the formula (1)
according to the invention are those wherein the ring A
is a cycloaliphatic radical of the formula (1a) or (1b); p,
r and s are 0; r is 0 or 1 and R and/or $R^1$ contains an
alkyl portion which is at most disubstituted; R only
denotes cyano, fluorine or chlorine if the ring bonded
directly to R is an aromatic radical of the formula (1c),
(1d) or (1e); there is at most one carboxyl group; at least
one of the bridge members $Z^1$, $Z^2$ or $Z^3$ is a covalent
bond; the structure is of formula (8)

 (8)

in which X, Y, A, B, $Z^1$, $R^1$, n, r and p are as defined
above; the rings A and B are radicals of the formulae
(1a), (1b) or/and (1c); the structure of formula (9)

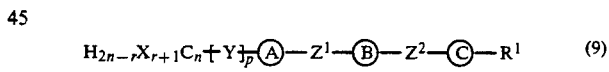 (9)

in which X, Y, A, B, C, $Z^1$, $Z^2$, $R^1$, n, p and r are as
defined above; the rings A, B and C denote radicals of
the formulae (1a), (1b) or/and (1c); none of the C atoms
of the end group of the formula H$_{2n-r}$X$_{r+1}$C$_n$[Y]$_p$,
which carries a radical X, is separated from the ring A
by more than two atoms of the end group chain; and R
or $R^1$ contains a substituted alkyl portion, wherein none
of the substituents is attached to a C atom of the alkyl
portion which is separated from the ring C or D by
more than two chain atoms of the end group chain.

In particular, the following features, individually or
in combination, are present:
the molecule contains two or not more than three
cyclic radicals and a total of 1 to not more than 4
cyano or halogen radicals;
the ring A is preferably a cycloaliphatic radical, in
particular one of the formula (1a);
the ring A preferably carries an XC$_{1-7}$-alkyl group, in
particular a cyano-C$_{1-7}$-alkyl group;
if X is halogen, fluorine and chlorine are preferred;

if R and/or $R^1$ contain a substituted alkyl portion, this preferably carries one or two substituents, preferred halogen atoms being fluorine and chlorine;

the molecule of the formula (1) preferably contains a total of at most one carboxyl group —COO— or —OOC—;

the molecule of the formula (1) preferably contains at most one aromatic ring of the formula (1c), (1d) or (1e);

the molecule of the formula (1) contains at least one bridge member Z in the form of a covalent bond;

the molecule of the formula (2) contains two or three cycloaliphatic radicals of the formulae (1a) and/or (1b);

if R and/or $R^1$ has an alkyl portion, this preferably contains 3 to 9 C atoms;

if R and/or $R^1$ is hydrogen or one of the X groups, the adjacent ring is an aromatic radical of the formula (1c), (1d), or (1e);

the radical X in the left end group and the substituent optionally present on the alkyl portion of R and/or $R^1$ are preferably attached to a C atom of the alkyl chain which is separated from the associated ring by not more than 2 C atoms.

The following formulae illustrate the structure of specific groups of compounds according to the invention, $A^1$, $B^1$ and $C^1$ in each case independently being the cycloaliphatic radicals (1a) or (1b), $A^2$, $B^2$ and $C^2$ in each case independently being the aromatic radicals (1c), (1d) or (1e), $R^4$ being $C_{1-12}$-alkyl, $C_{1-12}$-alkoxy, $XC_{1-7}$-alkyl, cyano, F or Cl and $R^5$ being $C_{1-12}$-alkyl, $C_{1-12}$alkoxy, $C_{1-12}$alkoxycarbonyl or $C_{1-12}$-alkylcarbonyloxy; and the symbols A, B, C, $Z^1$, $Z^2$, X and $R^1$ have the abovementioned meaning. Preferably $R^4$ and $R^5$ are $C_{1-12}$-alkyl. In formula $1_8$, the $B^2$ groups are identical.

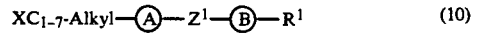 (10)

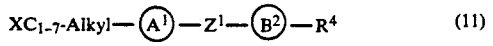 (11)

 (12)

 (13)

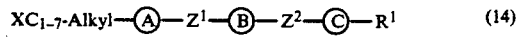 (14)

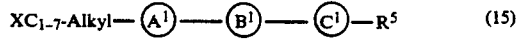 (15)

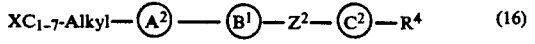 (16)

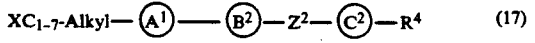 (17)

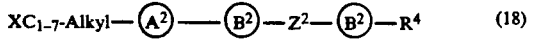 (18)

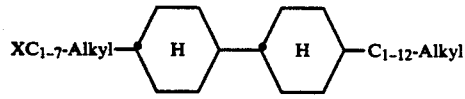 (19)

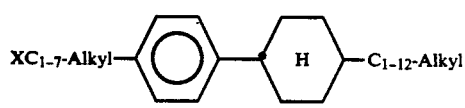 (20)

$XC_{1-7}$-Alkyl is a n-alkyl group having 1–7 C-atoms substituted by X. Preferably the substitution is at the end in ω-position. A preferred meaning of $XC_{1-7}$-Alkyl in particular is NC-$CH_2CH_2$-.

The invention also relates to liquid crystal mixtures which contain at least one compound of the formula (1), for example in amounts of 1–30 mol %, it being possible for the mixture also to contain several different compounds of the formula (1), for example in an amount of up to 90 mol % in total. As further components, the LC mixtures according to the invention can contain known anisotropic compounds and the additives corresponding to the intended use, such as dyestuffs, in particular pleochroic dyestuffs, optically active, or cholesteric components and the like. The preparation, compositions and use of the liquid crystal mixtures of this invention are fully routine and conventional. See, e.g., U.S. Pat. Nos. 3,995,941; 3,951,846 and 4,285,829. In view of the chiral properties of the compounds of this invention discussed above, they are advantageously useful as a chiral component (especially when in the smectic C phase) of ferroelectric liquid crystalline phases.

The new compounds of the formula (1) can be obtained by various methods which are known per se; a first general method is based, for example, on modifying a precursor corresponding to the molecule (1), without an X radical or without X-alkyl, by introduction of X or X-alkyl, for example by halogenation, such as bromination, if appropriate transhalogenation and if appropriate nitrilation, or by Friedel-Crafts reaction and reduction in a manner which is known per se.

A second general method is based, for example, on forming the molecule (1) by combining corresponding molecular fragments, for example by condensation, esterification or etherification on a bridge member.

Corresponding precursors or molecular fragments are either known as such or can be obtained analogously to the known compounds from known or conventionally preparable starting materials.

A general example for the first method is illustrated in equation V which follows; the chain length of the X-carrying end group can be further increased by repeating the steps; bromination/carboxylation/reduction/-bromination, the radical X in each case being terminal; the formation of an alkyl-end group with a non-terminal X, for example cyano, is illustrated in equation Va, in which case a "compound (1)",, that is to say a compound of the formula (1), or a corresponding "precursor" can in each case be used as the starting substance.

Equation Vb illustrates a specific example for the preparation of suitable "precursors-COOH", that is to say of corresponding carboxylic acids for the synthesis according to equation V or for the preparation of compounds of the formula (1) with terminal cyano on a ring by modification of the carboxyl group by known methods, for example directly or via the corresponding amide. "X-alkyl" in equation Vb here is a group of the formula $H_{2n'-r}X_{r+1}C_{n'}$—, in which n' is in each case one smaller than the n desired in formula (1).

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention.

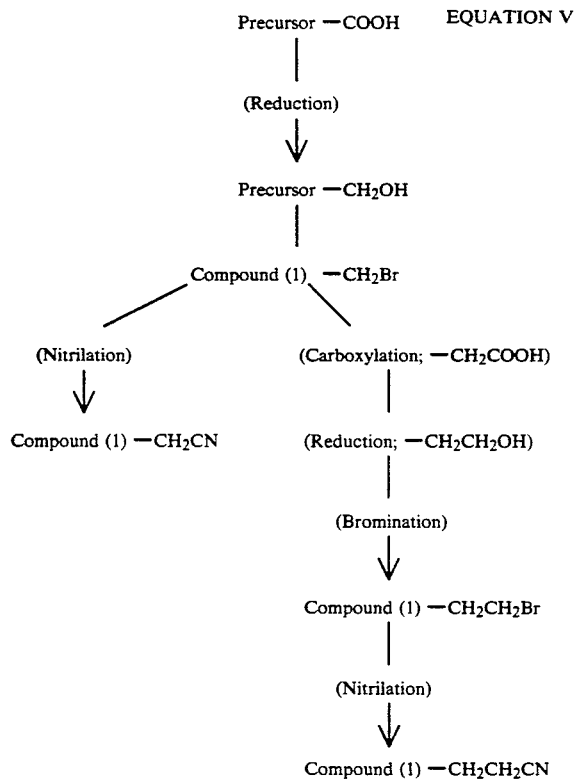

EQUATION V

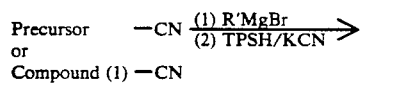

EQUATION Va

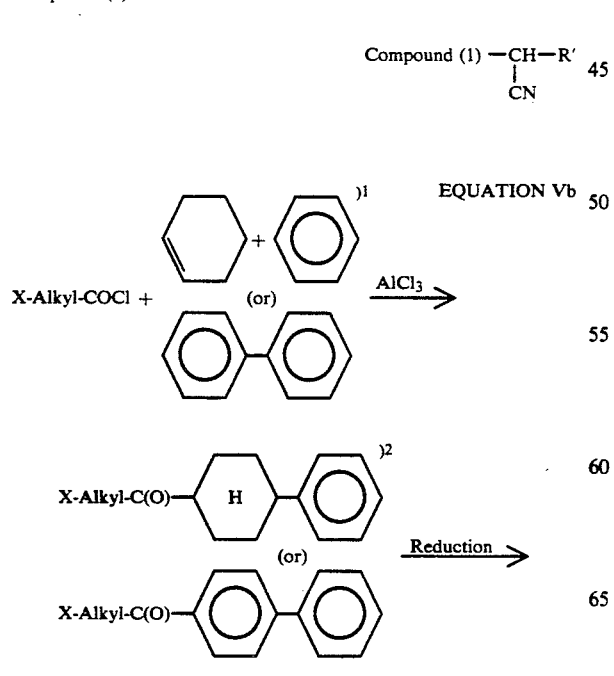

EQUATION Vb

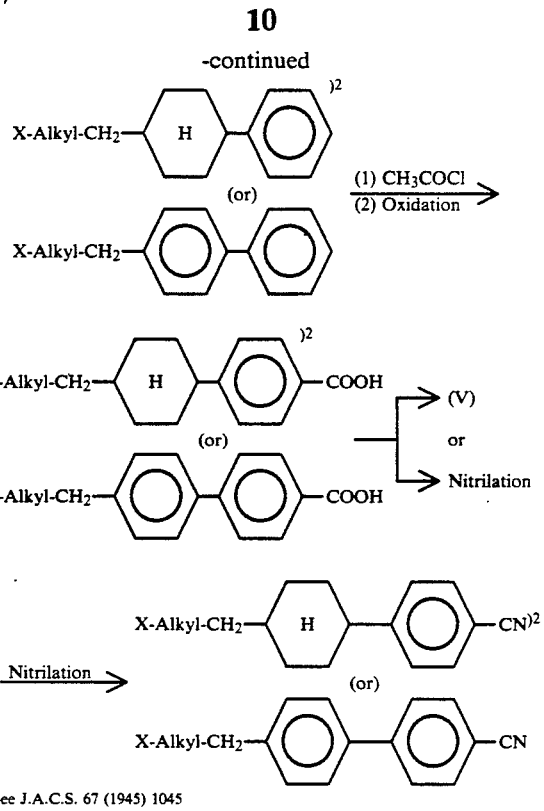

[1] See J.A.C.S. 67 (1945) 1045
[2] if appropriate, subsequent separation and isolation of the trans-isomers The reduction of the carboxyl compounds can be carried out with, for example, lithium aluminum hydride; the bromination is in most cases advantageously carried out with elemental bromine in the presence of triphenylphosphine, and the nitrilation is carried out, for example, with copper(I)-cyanide or KCN; the Grignard method or, in certain circumstances, nitrile group hydrolysis, is suitable for the carboxylation.

The following are general examples of known carboxyl-precursors or carboxyl-precursors which are obtainable in a known manner, $R^1$, B, C, $Z^1$ and $Z^2$ having the abovementioned meaning:

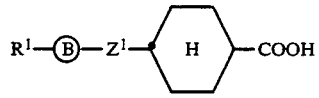 (V-1)

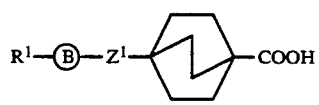 (V-2)

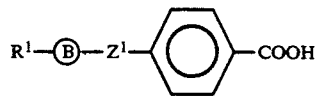 (V-3)

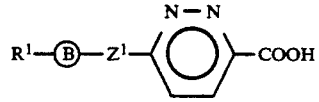 (V-4)

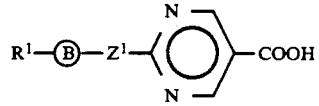 (V-5)

-continued

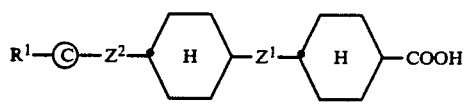   (V-6)

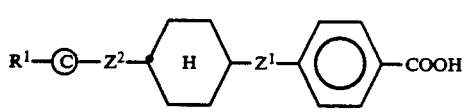   (V-7)

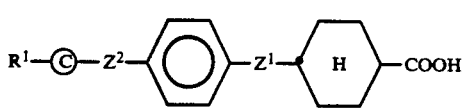   (V-8)

A general example of the second method for the preparation of compounds (1) according to the invention is illustrated in Equation VI below, in which the compound (1) to be prepared consists of two fragments, for example fragment$^a$ and fragment$^b$, which are bonded to one another by a bridge member Z, for example a carboxyl or methoxy group. Depending on the nature of the bridge group, the reaction is, for example, esterification, etherification or the like, and the fragment can carry a part ($Z^a$, $Z^b$) of the bridge to be formed; $L^1$ and $L^2$ are corresponding leaving groups.

EQUATION VI

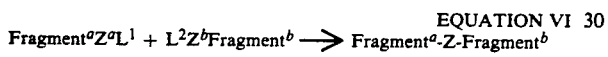

Suitable compounds for the synthesis according to Equation VI are also either known or can be obtained in a manner which is known per se. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsuis; unless otherwise indicated, all parts and percentages are by weight.

EXAMPLE 1

Preparation of 4-trans-cyanoethyl-cyclohexyl 4-trans-propyl-cyclohexyl-1-carboxylate 4-trans-propyl-cyclohexane-1-carboxylic acid (25 mmol) was warmed with thionyl chloride (40 ml) at the reflux temperature for 30 minutes. The acid chloride formed was freed from excess thionyl chloride. The acid chloride thus obtained was now added dropwise to a solution of 4-trans-cyanoethyl-cyclohexanol (melting point 52° C., 25 mmol, obtainable as follows: 2-(4-hydroxyphenyl)-propionamide was catalytically hydrogenated in 95% acetic acid (Nishimura catalyst). The resulting 1:1 cis-trans-mixture was equilibrated with aluminium isopropylate. The resulting trans alcohol was acetylated, converted to the nitrile by $SOCl_2$ and finally the acetyl group was hydrolized with NaOH) in 100 ml of pyridine. When the reaction had ended, the mixture was poured into excess dilute hydrochloric acid and extracted with methylene chloride. The product obtained from the extract by evaporation was recrystallized. The target compound of this example thus obtained is monotropically liquid crystal and has a melting point of 73.0° C. and a clear point of 14.6° C.

EXAMPLE 2

Preparation of 4-trans-cyanoethyl-cyclohexyl 4-trans-pentyl-cyclohexyl-1-carboxylate 4-trans-pentyl-cyclohexane-1-carboxylic acid (36.5 mmol) was boiled under reflux with thionyl chloride (50 ml) for 1 hour. The excess thionyl chloride was distilled. The resulting acid chloride was added dropwise to a solution of 36.5 mmol of 4-trans-cyanoethyl-cyclohexyl in 100 ml of pyridine. The reaction mixture was stirred until the reaction had ended and then poured onto dilute hydrochloric acid. The product was extracted with methylene chloride. For purification, the product was recrystallized. It has a monotropic liquid crystal phase and a melting point of 61.5° C. and a clear point of 39.3° C.

EXAMPLES 3-7

By the process described in Equation V or Va and from the corresponding carboxylic acids of the formula (30)

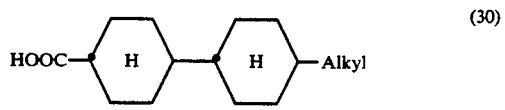   (30)

the compounds of the formula (31) according to the invention

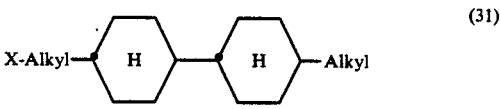   (31)

are prepared and their transition temperatures are determined.

The results are summarized in the following Table I

TABLE I

| Example | X-alkyl | alkyl | melting point | clear point (°C.) | |
|---|---|---|---|---|---|
| 3 | Br—$CH_2$—$CH_2$— | n-pentyl | 46.0 | 67.9 | |
| 4 | NC—$CH_2$—$CH_2$— | n-pentyl | 9 | 108.8 | |
| 5 | NC—$CH_2$— | n-pentyl | 56.5 | 82.6 | $\epsilon_\|$ 9.0 $\epsilon_\perp$ 8.5 |
| 6 | Br—$CH_2$— | n-propyl | 44.4 | (36.1) | |
| 7 | $H_3C(CH_2)_3C(H)(CN)$— | n-pentyl | 35 | 80.0 | |

EXAMPLE 7a

Preparation of 4-trans-cyanoethyl-4'-trans-propyl bicyclohexane according to Equation V Step 1: A solution of 4'-propyl-trans,trans-bicyclohexane-4-carboxylic acid (0.1M) [R. Eidenschink, D. Erdmann, J. Krause and L. Pohl, Angew. Che. Int. Ed. 17, 133 (1978)] in dry THF was added dropwise to a suspension of $LiAlH_4$ (10 g) in 100 ml of dry THF at 0°

C. The reaction mixture was then refluxed for 1 h, poured over cold dilute HCl and the product was extracted in ether.

Step 2: Bromine (0.12M) was added dropwise to a suspension of P(Ph)₃ (0.12M) in dry CH₃CN at 0° C. and the mixture stirred for 30 min at room temperature. To this suspension, a solution of the alcohol prepared above in dry CH₃CN was added dropwise and the mixture stirred for 15 min at this temperature. The solvent was then distilled off and the reactants heated for 30 min at 130° C. After usual working up the reaction mixture, the raw product was extracted in CH₂Cl₂ and the solution was added to hexane to precipitate the triphenylphosphine oxide. The product was purified by chromatography (silica gel/toluene).

Step 3: A solution of the above prepared bromide in dry ether was added dropwise to a suspension of magnesium (4 g) in dry ether and the mixture stirred at room temperature for 1 h. Dry CO₂ gas was then passed through the reaction mixture for 30 min, before it was worked up in the usual way. The raw product was crystallized from toluene or hexane. Steps 1 and 2 were then repeated using this product as a starting material.

Step 4: A mixture of the so prepared 4-trans-bromoethyl-4'-trans-propyl bicyclohexane and solid KCN was heated at 100° C. for 2 h in DMSO and then poured onto water. The reaction product was extracted in ether and filtered through a short silica gel column using toluene as a solvent. It was crystallized from EtOH, melting point 13° C., clear point 99° C.

EXAMPLES 8–12

By the process according to Equation V or Va and from the corresponding carboxylic acids of the formula (80)

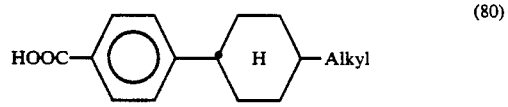

(80)

the corresponding compounds of the formula (81) according to the invention

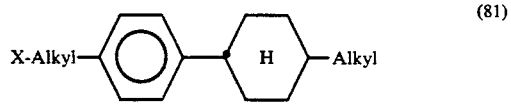

(81)

are prepared. The resulting anisotropic compounds are summarised in the following Table II.

TABLE II

| Example | X-alkyl | alkyl | melting point | clear point (°C.) |
|---|---|---|---|---|
| 8 | Br—CH₂—CH₂— | n-pentyl | 30 | |
| 9 | I—CH₂—CH₂— | n-pentyl | 36.2 | |
| 10 | NC—CH₂—CH₂— | n-pentyl | 44.8 | (28.3) |
| 11 | B—CH₂— | n-pentyl | 28.6 | |
| 12 | H₃C(CH₂)₃C(H)(CN)— | n-pentyl | 34 | |

EXAMPLE 13

Preparation of 4-cyanoethylphenyl-4-trans-pentyl-cyclohexyl-1-carboxylate

A solution of trans-4-pentylcyclohexane carboxylic acid chloride (0.1M) in pyridine, was added dropwise to a stirred solution of 4-trans-cyanoethyl-cyclohexanol (0.1M) in pyridine at 0–5° C., and the mixture stirred at this temperature for 2 h. The reaction mixture was then worked up in the usual way and the product crystallized twice from methanol, melting point 75° C., clear point 51° C.

Other examples of compounds of the formula (1) are the following. They can be prepared as described above.

4-fluoromethyl-4'-pentyl-biphenyl
4-fluoromethyl-4'-cyano-biphenyl
4-(2-fluoroethyl)-4'-cyano-biphenyl
4-(2-chloroethyl)-4'-bromo-biphenyl
4-(2-chloroethyl)-4'-(2-cyanoethyl)-biphenyl
4,4'-bis-(2-chloroethyl)-biphenyl
4,4'-bis-(2-fluoroethyl)-biphenyl
4-(3-fluoropropyl)-4'-cyano-biphenyl
4-(3-chloropropyl)-4'-butoxy-biphenyl
4-(3-(fluoropropyl)-4'-bromo-biphenyl
4-(3-cyanopropyl)-4-pentyl-biphenyl
4-(3-cyanopropyl)-4-fluoromethyl-biphenyl
4-(3-chloropropyl)-4-(2-fluoroethyl)-biphenyl
4-(3-fluoropropyl)-4-(3-bromopropyl)-biphenyl
4-(3-cyanopropyl)-4-(3-fluoropropyl)-biphenyl
4,4'-bis-(3-cyanopropyl)-biphenyl
4,4'-bis-(3-chloropropyl)-biphenyl
4,4'-bis-(3-bromopropyl)-biphenyl
4,4'-bis-(3-fluoropropyl)-biphenyl
4-(4-cyanobutyl-4'-cyano-biphenyl
4-(4-chlorobutyl)-4'-bromo-biphenyl
4-(4-fluorobutyl)-4'-butoxy-biphenyl
4-(4-bromobutyl)-4'-fluoro-biphenyl
4,4'-bis-(4-cyanobutyl)-biphenyl
4,4'-bis-(4-chlorobutyl)-biphenyl
4,4'-bis-(4-fluorobutyl)-biphenyl
4,4'-bis-(4-bromobutyl)-biphenyl
4-(4-cyanobutyl)-4'-(2-cyanoethyl)-biphenyl
4-(4-cyanobutyl)-4'-(4-fluorobutyl)-biphenyl
4-(4-chlorobutyl)-4'-(3-fluoropropyl)-biphenyl
4-(4-fluorobutyl)-4'-cyano-biphenyl
4-(2-fluorobutyl)-4'-cyano-biphenyl
4-(1-fluoropentyl)-4'-cyano-biphenyl
4-(2-fluoropentyl)-4'-cyano-biphenyl
4-(3-fluoropentyl)-4'-cyano-biphenyl
4-(5-fluoropentyl)-4'-cyano-biphenyl
4-fluoromethyl-4''-butoxy-p-terphenyl
4-fluoromethyl-4''-fluoro-p-terphenyl
4-fluoromethyl-4''-cyano-p-terphenyl
4-cyanomethyl-4''-pentyl-p-terphenyl
4,4''-bis-(fluoromethyl)-p-terphenyl
4-(2-fluoroethyl)-4''-cyano-p-terphenyl
4-(2-chloroethyl)-4''-butoxy-p-terphenyl
4-(2-fluoroethyl)-4''-chloro-p-terphenyl
4-(2-cyanoethyl)-4''-chloro-p-terphenyl
4-(2-cyanoethyl)-4''-(3-fluoropropyl)-p-terphenyl
4-(2-chloroethyl)-4''-(2-fluoropropyl)-p-terphenyl
4-(2-bromoethyl)-4''-cyanomethyl-p-terphenyl
4-(2-fluoroethyl)-4''-bromomethyl-p-terphenyl
4,4''-bis-(2-chloroethyl)-p-terphenyl
4,4''-bis-(2-fluoroethyl)-p-terphenyl
4,4''-bis-(2-bromoethyl)-p-terphenyl
4,4''-bis-(2-cyanoethyl)-p-terphenyl
4-(1-fluoropentyl)-4''-cyano-p-terphenyl
4-(2-fluoropropyl)-4''-cyano-p-terphenyl
4-(3-fluoropropyl)-4''-cyano-p-terphenyl
4-(5-fluoropentyl)-4''-cyano-p-terphenyl
4-(3-chloropropyl)-4''-pentyl-p-terphenyl 4-(3-chloropropyl)-4'''-chloromethyl-p-terphenyl
4-(3-bromopropyl)-4'''-(2-fluoroethyl)-p-terphenyl
4-(3-cyanopropyl)-4'''-(3-chloropropyl)-p-terphenyl
4,4'''-bis-(3-cyanopropyl)-p-terphenyl
1-(4-fluoromethylphenyl)-2-(4-cyanophenyl)-ethane
1-(4-cyanoethyl)-phenyl)-2-(4-pentylphenyl)-ethane
1-(4-(3-chloropropyl)-phenyl)-2-(4-cyanomethyl-phenyl)-ethane
1-(4-(4-bromobutyl)-phenyl)-2-(4-(3-cyanopropyl)-phenyl-ethane
1-(4-(3-fluoropropyl)-phenyl)-2-(4-cyanophenyl)-ethane
1-(4-(3-fluoropropyl)-phenyl)-2-(4-(2-cyanoethyl)-phenyl)-ethane
1,2-bis-(4-fluoromethylphenyl)-ethane
1,2-bis-(4-(4-cyanobutyl)-phenyl)-ethane
4,4''-bis-(4-cyanobutyl)-p-terphenyl
4,4''-bis-(4-chlorobutyl)-p-terphenyl
4'-(4-chlorobutyl)-4''-butoxy-p-terphenyl
1-(4-trans-(1-fluoropentyl)-cyclohexyl)-4-cyano-benzene
1-(4-trans-fluoromethyl-cyclohexyl)-4-cyano-benzene
1-(4-trans-(5-fluoropentyl)-cyclohexyl)-4-cyano-benzene
1-(4-trans-(2-cyanoethyl)-cyclohexyl)-4-butoxy-benzene
1-(4-trans-(3-chloropropyl)-cyclohexyl)-4-(2-cyanoethyl)-benzene
1-(4-trans-(4-bromobutyl)-cyclohexyl)-4-(3-fluoropropyl)-benzene
1-(4-trans-(4-chlorobutyl)-cyclohexyl)-4-pentyl-benzene
1-(4-trans-(3-fluoropropyl)-cyclohexyl)-4-(3-fluoropropyl)-benzene
1-(4-trans-(2-fluoropentyl)-cyclohexyl)-4-cyano-benzene
1-(4-trans-(3-fluoropentyl)-cyclohexyl)-4-cyano-benzene
1-(4-trans-(2-cyanoethyl)-cyclohexyl)-2-(4-cyanophenyl)-ethane
1-(4-trans-(3-fluoropropyl)-cyclohexyl)-2-(4-(2-cyanoethyl)-phenyl)-ethane
1-(4-trans-(4-chlorobutyl)-cyclohexyl)-2-(4-pentylphenyl)-ethane
1-(4-trans-fluoromethyl-cyclohexyl)-2-(4-butoxyphenyl)-ethane
4-(4-trans-(2-cyanoethyl)-cyclohexyl)-4'-(3-fluoropropyl)-biphenyl
4-(4-trans-(3-fluoropropyl)-cyclohexyl)-4'-cyano-biphenyl
4-(4-trans-(5-fluoropentyl)-cyclohexyl)-4'-cyano-biphenyl
4-(4-trans-(cyanomethyl-cyclohexyl)-4'-pentyl-biphenyl
4-(4-trans-(fluoromethyl-cyclohexyl)-4'-fluoromethyl-biphenyl
1-(4-trans-(2-chloroethyl)-cyclohexyl)-2-(4'-butoxybiphenyl-4-yl)-ethane
1-(4-trans-(3-fluoropropyl)-cyclohexyl)-2-(4'-cyanobiphenyl-4-yl)-ethane
1-(4-trans-(4-cyanobutyl)-cyclohexyl)-2-(4'-(3-fluoropropyl)-biphenyl-4-yl)-ethane
1-(4-trans-(bromoethyl-cyclohexyl)-2-(4'-(2-cyanoethyl)-biphenyl-4-yl)-ethane
1-(4-fluoromethyl-1-bicyclo-(2,2,2)-octyl)-4-cyano-benzene
1-(4-(2-chloroethyl)-1-bicyclo-(2,2,2)-octyl)-4-pentyl-benzene
1-(4-(3-cyanopropyl)-1-bicyclo-(2,2,2)-octyl)-4-(3-fluoropropyl)-benzene
1-(4-(4-bromobutyl)-1-bicyclo-(2,2,2)-octyl)-4-butoxy-benzene
4-(4-fluoromethyl-1-bicyclo-(2,2,2)-octyl)-4'-pentyl-biphenyl
4-(4-(2-cyanoethyl)-1-bicyclo-(2,2,2)-octyl)-4'-(3-fluoropropyl)-biphenyl
4-(4-(3-bromopropyl)-1-bicyclo-(2,2,2)-octyl)-4'-(2-cyanoethyl)-biphenyl
4-(4-(4-chlorobutyl)-1-bicyclo-(2,2,2)-octyl)-4'-butoxybiphenyl
4-(4-(3-fluoropropyl)-1-bicyclo-(2,2,2)-oxtyl)-4'-cyanobiphenyl
3-(4-(3-fluoropropyl)-phenyl)-6-pentyl-pyridazine
3-(4-(2-cyanoethyl)-phenyl)-6-butoxy-pyridazine
3-(4-(3-chloropropyl)-phenyl)-6-butoxy-pyridazine
1-(4-fluoromethylphenyl)-2-(6-pentylpyridazin-3-yl)-ethane
1-(4-(2-cyanoethyl)-phenyl)-2-(6-butoxypyridazin-3-yl)-ethane
1-(4-(3-bromopropyl)-phenyl)-2-(6-butoxypyridazin-3-yl)-ethane
1-(4-(4-chlorobutyl)-phenyl)-2-(6-pentylpyridazin-3-yl)-ethane
3-(4-fluoromethylphenyl)-6-(4-pentylphenyl)-pyridazine
3-(4-(2-chloroethyl)-phenyl)-6-(4-butoxyphenyl)-pyridazine
3-(4-(3-fluoropropyl)-phenyl)-6-(4-pentylphenyl)-pyridazine
3-(4-(4-cyanobutyl)-phenyl)-6-(4-butoxyphenyl)-pyridazine
3-(4-(4-cyanobutyl)-phenyl)-6-(4-pentylphenyl)-pyridazine
3-(4-(3-fluoropentyl)-phenyl)-6-(4-cyanophenyl)-pyridazine
3-(4-trans-(bromomethyl-cyclohexyl)-6-(4-butoxyphenyl)-pyridazine
3-(4-trans-(2-cyanoethyl)-cyclohexyl)-6-(4-pentylphenyl)-pyridazine
3-(4-trans-(3-chloropropyl)-cyclohexyl)-6-(4-butoxyphenyl)-pyridazine
3-(4-trans-(4-bromobutyl)-cyclohexyl)-6-(4-pentylphenyl)-pyridazine
3-(4-trans-(4-fluorobutyl)-cyclohexyl)-6-(4-cyanophenyl)-pyridazine
3-(2-(4-trans-cyanomethyl-cyclohexyl)-ethyl)-6-(4-pentyl-phenyl)-pyridazine
3-(2-(4-trans-(2-chloroethyl)-cyclohexyl)-ethyl)-6-(4-butoxyphenyl)-pyridazine
3-(2-(4-trans-(3-fluoropropyl)-cyclohexyl)-ethyl)-6-(4-pentylphenyl)-pyridazine
3-(2-(4-trans-(4-bromobutyl)-cyclohexyl)-ethyl)-6-(4-butoxyphenyl)-pyridazine
3-(2-(4-trans-(5-fluoropentyl)-cyclohexyl)-ethyl)-6-(4-cyanophenyl)-pyridazine
3-(4-trans-chloromethyl-cyclohexyl)-6-pentyl-pyridazine
3-(4-trans-(2-cyanoethyl)-cyclohexyl)-6-butoxy-pyridazine
3-(4-trans-(3-fluoropropyl)-cyclohexyl)-6-butoxy-pyridazine
3-(4-trans-(4-bromobutyl)-cyclohexyl)-6-pentyl-pyridazine
1-(4-trans-cyanomethyl-cyclohexyl)-2-(6-pentyl-3-pyridazine)-ethane 1-(4-trans-(2-bromoethyl)-cyclohexyl)-2-(6-butoxy-3-pyridazine)-ethane
1-(4-trans-(3-chloropropyl)-cyclohexyl)-2-(6-pentyl-3-pyridazine)-ethane
1-(4-trans-(4-fluorobutyl)-cyclohexyl)-2-(6-butoxy-3-pyridazine)-ethane
1-(4-trans-(3-fluoropropyl)-cyclohexyl)-2-(6-butoxy-3-pyridazine)-ethane
2-(4-cyanophenyl)-5-(3-fluoropropyl)-pyrimidine
2-(4-(2-cyanoethyl)-phenyl)-5-(2-chloroethyl)-pyrimidine
2-(4-(3-chloropropyl)-phenyl)-5-pentyl-pyrimidine
2-(4-(4-fluorobutyl)-phenyl)-5-(2-cyanoethyl)-pyrimidine
2-(4-(fluoromethylphenyl)-5-(4-cyanophenyl)-pyrimidine
2-(4-fluoromethylphenyl)-5-(4-(2-fluoroethyl)-phenyl)-pyrimidine
2-(4-(2-bromoethyl)-phenyl)-5-(4-pentylphenyl)-pyrimidine
2-(4-(3-chloropropyl)-phenyl)-5-(4-(3-fluoropropyl)-phenyl)-pyrimidine
2-(4-(4-trans-bromomethyl-cyclohexyl)-phenyl)-5-pentyl-pyrimidine
2-(4-(4-trans-(2-chloroethyl)-cyclohexyl)-phenyl)-5-(3-fluoropropyl)-pyrimidine
2-(4-(4-trans-(3-fluoropropyl)-cyclohexyl)-phenyl)-5-(2-bromoethyl)-pyrimidine
2-(4-(4-trans-(4-cyanobutyl)-cyclohexyl)-phenyl)-5-(4-cyanobutyl)-pyrimidine
2-(4-(4-trans-(4-fluorobutyl)-cyclohexyl)-phenyl)-5-pentyl-pyrimidine
2-(4-(4-trans-cyanomethyl-cyclohexyl)-phenyl)-5-pentyl-pyrimidine
1-(4-trans-chloromethyl-cyclohexyl)-2-(4-(5-pentyl-2-pyrimidine)-phenyl)-ethane
1-(4-trans-(2-cyanoethyl)-cyclohexyl)-2-(4-(5-(2-chloroethyl)-2-pyrimidine)-phenyl)-ethane
1-(4-trans-(3-fluoropropyl)-cyclohexyl)-2-(4-(5-(3-bromopropyl)-2-pyrimidine)-phenyl)-ethane
1-(4-trans-(4-bromobutyl)-cyclohexyl)-2-(4-(5-butoxy-2-pyrimidine)-phenyl)-ethane
1-(4-trans-(2-cyanoethyl)-cyclohexyl)-2-(4-(5-(3-fluoropropyl)-2-pyrimidine)-phenyl)-ethane
4-trans-cyanomethyl-4'-trans-propyl-bicyclohexane
4-trans-(2-bromoethyl)-4'-trans-propyl-bicyclohexane
4-trans-(3-fluoropropyl)-4'-trans-pentyl-bicyclohexane
4-trans-(2-cyanoethyl)-4'-trans-propyl-bicyclohexane
4-trans-(2-cyanoethyl)-4'-trans-pentyl-bicyclohexane
4-trans-(2-bromoethyl)-4'-trans-pentyl-bicyclohexane
4-trans-bromomethyl-4'-trans-propyl-bicyclohexane
4-trans-bromomethyl-4'-trans-pentyl-bicyclohexane
4-trans-cyanomethyl-4'-trans-pentyl-bicyclohexane
4-trans-(4-bromobutyl)-4'-trans-pentyl-bicyclohexane
4-trans-(4-cyanobutyl)-4'-trans-propyl-bicyclohexane
4-trans-chloromethyl-4'-trans-propyl-bicyclohexane
4-trans-(2-chloroethyl)-4'-trans-pentyl-bicyclohexane
1-(4-trans-cyanomethyl-cyclohexyl)-2-(4-trans-pentyl-cyclohexyl)-ethane
1-(4-trans-(2-chloroethyl)-cyclohexyl)-2-(4-trans-propylcyclohexyl)-ethane
1-(4-trans-(3-fluoropropyl)-cyclohexyl)-2-(4-trans-pentyl-cyclohexyl)-ethane
1-(4-trans-(4-cyanobutyl)-cyclohexyl)-2-(4-trans-pentyl-cyclohexyl)-ethane
1-(4-trans-(4-bromobutyl)-cyclohexyl)-2-(4-trans-propylcyclohexyl)-ethane
4-bromomethyl-4″-propyl-p-ter-trans-cyclohexane
4-(2-chloroethyl)-4″-pentyl-p-ter-trans-cyclohexane
4-(3-fluoropropyl)-4″-propyl-p-ter-trans-cyclohexane
4-(4-cyanobutyl)-4″-pentyl-p-ter-trans-cyclohexane
1-(4-trans-cyanomethyl-cyclohexyl)-4-propyl-bicyclo-(2,2,2)-octane
1-(4-trans-(2-bromoethyl)-cyclohexyl)-4-pentyl-bicyclo-(2,2,2)-octane
1-(4-trans-(3-fluoropropyl)-cyclohexyl)-4-propyl-bicyclo-(2,2,2)-octane
1-(4-trans-(4-chlorobutyl)-cyclohexyl)-4-pentyl-bicyclo-(2,2,2)-octane
1-(4-trans-chloromethyl-cyclohexyl)-2-(4-propyl-1-bicyclo-(2,2,2)-octyl)-ethane
1-(4-trans-(2-bromoethyl)-cyclohexyl)-2-(4-pentyl-1-bicyclo-(2,2,2)-octyl)-ethane
1-(4-trans-(3-cyanopropyl)-cyclohexyl)-2-(4-propyl-1-bicyclo-(2,2,2)-octyl)-ethane
1-(4-trans-(4-fluorobutyl)-cyclohexyl)-2-(4-pentyl-1-bicyclo-(2,2,2)-octyl)-ethane
4-trans-fluoromethyl-4″-trans-(4-propyl-1-bicyclo-(2,2,2)-octyl)-bicyclohexane
4-trans-(2-cyanoethyl)-4″-trans-(4-pentyl-1-bicyclo-(2,2,2)-octyl)-bicyclohexane
4-trans-(3-chloropropyl)-4″-trans-(4-propyl-1-bicyclo-(2,2,2)-octyl)-bicyclohexane
4-trans-(4-bromobutyl)-4″-trans-(4-pentyl-1-bicyclo-(2,2,2)-octyl)-bicyclohexane
4-trans-(4-fluorobutyl)-4″-trans-(4-pentyl-1-bicyclo-(2,2,2)-octyl)-bicyclohexane
4-trans-(3-cyanopropyl)-4″-trans-(4-pentyl-1-bicyclo-(2,2,2)-octyl)-bicyclohexane
4-trans-(2-bromoethyl)-4″-trans-(4-propyl-1-bicyclo-(2,2,2)-octyl)-bicyclohexane
4-trans-fluoromethyl-cyclohexyl 4-butoxy-benzoate
4-trans-(2-cyanoethyl)-cyclohexyl 4-cyano-benzoate
4-trans-(2-cyanoethyl)-cyclohexyl 4-pentyl-benzoate
4-trans-(3-fluoropropyl)-cyclohexyl 4-(2-cyanoethyl)-benzoate
4-trans-(4-bromobutyl)-cyclohexyl 4-chloro-benzoate
1-(4-trans-chloromethyl-cyclohexyl)-methoxy-4-pentylbenzene
1-(4-trans-(2-cyanoethyl)-cyclohexyl)-methoxy-4-butoxy-benzene
1-(4-trans-(3-bromopropyl)-cyclohexyl)-methoxy-4-cyano-benzene
1-(4-trans-(4-fluorobutyl)-cyclohexyl)-methoxy-4-fluoro-benzene
4-trans-bromomethyl-cyclohexyl 4-trans-(4-pentylphenyl)-cyclohexane-1-carboxylate
4-trans-(2-cyanoethyl)-cyclohexyl 4-trans-(4-butoxyphenyl)-cyclohexane-1-carboxylate
4-trans-(3-chloropropyl)-cyclohexyl 4-trans-(4-cyanophenyl)-cyclohexane-1-carboxylate
4-trans-(4-fluorobutyl)-cyclohexyl 4-trans-(4-chlorophenyl)-cyclohexane-1-carboxylate
1-(4-trans-(4-pentylphenyl)-cyclohexyl)-methoxy-4-trans-cyanomethyl-cyclohexane
1-(4-trans-(4-butoxyphenyl)-cyclohexyl)-methoxy-4-trans-(2-bromoethyl)-cyclohexane
1-(4-trans-(4-cyanophenyl)-cyclohexyl)-methoxy-4-trans-(3-fluoropropyl)-cyclohexane
1-(4-trans-(4-fluorophenyl)-cyclohexyl)-methoxy-4-trans-(4-chlorobutyl)-cyclohexane
4-trans-chloromethyl-cyclohexyl 4-(4-trans-pentyl-cyclohexyl)-benzoate
4-trans-(2-cyanoethyl)-cyclohexyl 4-(4-trans-(2-cyanoethyl)-cyclohexyl)-benzoate 4-trans-(3-bromopropyl)-cyclohexyl 4-(4-trans-(3-fluoropropyl)-cyclohexyl)-benzoate
4-trans-(4-fluorobutyl)-cyclohexyl 4-(4-trans-(4-chlorobutyl)-cyclohexyl)-benzoate
4-trans-(2-cyanoethyl)-cyclohexyl 4-(4-trans-pentyl-cyclohexyl)-benzoate
1-(4-trans-bromomethyl-cyclohexyl)-4-(4-trans-cyanomethyl-cyclohexyl)-methoxy-benzene
1-(4-trans-pentyl-cyclohexyl)-4-(4-trans-(2-bromoethyl)-cyclohexyl)-methoxy-benzene
1-(4-trans-(2-cyanoethyl)-cyclohexyl)-4-(4-trans-(3-fluoropropyl)-cyclohexyl)-methoxy-benzene
1-(4-trans-(3-chloropropyl)-cyclohexyl)-4-(4-trans-(4-bromobutyl)-cyclohexyl)-methoxy-benzene
4-trans-(fluoromethyl)-cyclohexyl-4'-(2-cyanoethyl)-bicyclohexane-4-carboxylate
4-trans-(2-cyanoethyl)-cyclohexyl-4'-(3-fluoropropyl)-bicyclohexane-4-carboxylate
4-trans-(3-chloropropyl)-cyclohexyl-4'-(pentyl)-bicyclo-hexane-4-carboxylate
4-trans-(4-bromobutyl)-cyclohexyl-4'-(2-chloroethyl)-bicyclohexane-4-carboxylate
1-(4'-pentylbicyclohex-4-yl)-methoxy-4-trans-fluoromethyl-cyclohexane
1-(4'-(2-cyanoethyl)-bicyclohex-4-yl)-methoxy-4-trans-(2-cyanoethyl)-cyclohexane
1-(4'-(3-fluoropropyl)-bicyclohex-4-yl)-methoxy-4-trans-(3-fluoropropyl)-cyclohexane
1-(4'-(4-chlorobutyl)-bicyclohex-4-yl)-methoxy-4-trans-(4-bromobutyl)-cyclohexane
4-trans-bromomethyl-cyclohexyl-4-pentyl-bicyclo-(2,2,2)-octane-1-carboxylate
4-trans-(2-cyanoethyl)-cyclohexyl-4-(2-cyanoethyl)-bicyclo-(2,2,2)-octane-1-carboxylate
4-trans-(3-chloropropyl)-cyclohexyl-4-(3-fluoropropyl)-bicyclo-(2,2,2)-octane-1-carboxylate
4-trans-(4-fluorobutyl)-cyclohexyl-4-(4-cyanobutyl)-bicyclo-(2,2,2)-octane-1-carboxylate
1-(4-pentyl-1-bicyclo-(2,2,2)-octyl)-methoxy-4-trans-cyanomethyl-cyclohexane
1-(4-(2-cyanoethyl)-1-bicyclo-(2,2,2)-octyl)-methoxy-4-trans-(2-cyanoethyl)-cyclohexane
1-(4-(3-fluoropropyl)-1-bicyclo-(2,2,2)-octyl)-methoxy-4-trans-(3-chloropropyl)-cyclohexane
1-(4-(4-chlorobutyl)-bicyclo-(2,2,2)-octyl)-methoxy-4-trans-(4-fluorobutyl)-cyclohexane Examples of liquid crystal mixtures according to the invention:

EXAMPLE A

A liquid crystal mixture is prepared from
9% 2-p-cyanophenyl-5-propyl-1,3-dioxane
12% 2-p-cyanophenyl-5-butyl-1,3-dioxane
9% 2-p-cyanophenyl-5-pentyl-1,3-dioxane
6% 2-p-octoxyphenyl-5-pentyl-pyrimidine
5% 2-p-nonoxyphenyl-5-pentyl-pyrimidine
5% 2-p-heptoxyphenyl-5-hexyl-pyrimidine
4% 2-p-nonoxyphenyl-5-hexyl-pyrimidine
6% 4,4'-bis-(trans-4-propylcyclohexyl)-biphenyl
9% 4-(trans-4-pentylcyclohexyl)-4'-(trans-4-propylcyclohexyl)-biphenyl
17% r-1-cyano-1-pentyl-cis-4-(trans-4-propylcyclohexyl)-cyclohexane and
18% 4-trans-cyanoethyl-4'-trans-propylbicyclohexane.

EXAMPLE B

A liquid crystal mixture is prepared from
27% trans,trans-4-pentylcyclohexylcyclohexane-4'-carbonitrile 17% trans,trans-4-propylcyclohexylcyclohexane-4'-carbonitrile
30% 4-trans-cyanoethyl-4'-trans-pentyl-bicyclohexane
16% trans-4-propylcyclohexanecarboxylic acid (p-ethoxyphenylester) and
10% trans,trans-4-pentyl-4'-butyryloxybicyclohexane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. In a liquid crystalline mixture comprising at least two liquid crystalline components, the improvement wherein at least one of said components is a compound of formula (1)

wherein the rings A and B are different and each is a cycloaliphatic radical of the formula (1a) or (1b)

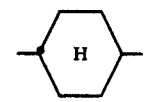

(1a)

(1b)

or an aromatic radical of the formula (1c), (1d) or (1e)

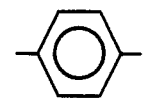

(1c)

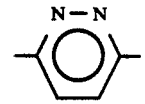

(1d)

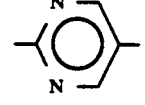

(1e)

X is cyano or halogen;
Y is —O—, —C(O)O—, —O(O)C—, or —NH—;
$Z^1$ is a covalent bond, —COO—, —OOC—, —CH$_2$O—, or —CH$_2$—CH$_2$—;
n is an integer from 4 to 12;
p is 0 or 1; and
R is alkyl, alkoxy, alkoxycarbonyl, alkylcarbonyloxy or alkylamino, the alkyl part of which in each case contains 1 to 12 C atoms, with the provisos that (a) when an oxygen atom is bonded directly to one of the cycloaliphatic radicals of the formula (1a) or (1b) present in the molecule, then no other oxygen atom and no nitrogen atom or radical X is bonded directly to that cycloaliphatic radical, (b) no groups of formulae —CH$_2$O— or —C(X)(-H)— are bonded directly to any of the aromatic radicals of the formulae (1c), (1d) or (1e) present in the molecule, except when X is fluorine; and (c) H$_{2n}$XC$_n$ is an alkyl-end group with a non-terminal X.

2. A mixture of claim 1, wherein in formula (1), the ring A in formula (1) is a cycloaliphatic radical of the formula (1a) or (1b).

3. A mixture of claim 1, wherein in formula (1), p is 0.

4. A mixture of claim 1, wherein in formula (1), the ring A is an aromatic radical of the formula (1c), (1d) or (1e).

5. A mixture of claim 1, wherein the compound of the formula (1) contains at most one —COO— or —OOC— group.

6. A mixture of claim 1, wherein in formula (1), Z$^1$ Z is a covalent bond.

7. A mixture of claim 1, wherein X is cyano.

8. A mixture of claim 1, wherein n is 4 or 5.

9. A mixture of claim 1, wherein in formula (1) the C atom of the end group of the formula H$_{2n}$XC$_n$[Y]$_p$, which carries the n on-terminal radical X, is separated from the ring A by not more than two C atoms of the end group chain.

10. A mixture of claim 1 wherein in formula (1) halo is F or Cl.

11. A mixture of claim 1, wherein the compound of formula (I) is chiral.

12. A mixture of claim 1, wherein R is chiral.

13. In an electrooptical display element, based on a liquid crystal mixture, the improvement wherein the mixture is one of claim 1.

14. In a liquid crystalline mixture comprising at least two liquid crystalline components, at least one component comprising (a) two to four six-membered rings linked to each other or to end groups by optional bridging groups, at least two of said rings being different, and (b) end groups attached at each end of said (a) portion, the improvement wherein at least one of said end groups is of the formula —C$_n$XH$_{2n}$, wherein n is 4–12 and X is attached to a non-terminal position and is cyano or halogen.

15. A dielectric of claim 14, wherein n is 4 or 5.

16. A dielectric of claim 14, wherein X is F or Cl.

17. A dielectric of claim 15, wherein X is F or Cl.

18. A dielectric of claim 16, wherein the group C$_n$XH$_{2n}$ has the structure

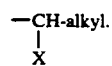

19. A dielectric of claim 15, wherein the group C$_n$XH$_{2n}$ has the structure

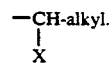

20. A dielectric of claim 16, wherein the group C$_n$XH$_{2n}$ is a straight chain X-substituted alkyl group.

21. A dielectric of claim 16, wherein the group C$_n$XH$_{2n}$ is a branched X-substituted alkyl group.

22. A dielectric of claim 21, wherein the group C$_n$XH$_{2n}$ is a straight chain X-substituted alkyl group.

23. A dielectric of claim 21, wherein the group C$_n$XH$_{2n}$ is a branched X-substituted alkyl group.

24. A dielectric of claim 14, wherein portion (a) comprises two or three of said six-membered rings.

25. A dielectric of claim 14, wherein said optional bridging groups are —COO—, —OOC—, —CH$_2$O—, —OCH$_2$— or —CH$_2$CH$_2$—.

26. A dielectric of claim 24, wherein said optional bridging groups are —COO—, —OOC—, —CH$_2$O—, —OCH$_2$— or —CH$_2$CH$_2$—.

* * * * *

UNITED STATES PATENT AND TRADEMARK OFFICE
CERTIFICATE OF CORRECTION

PATENT NO. : 5,120,467
DATED : June 9, 1992
INVENTOR(S) : Tuong HUYNH-BA et al.

It is certified that error appears in the above-identified patent and that said Letters Patent is hereby corrected as shown below:

Col. 22; Lines 8-11; Lines 18, 25, 27, 29, 31, 33, 35, 38;

Claims 15-26: Change "dielectric" in each of these claims to --mixture--.

Signed and Sealed this

Twelfth Day of July, 1994

Attest:

BRUCE LEHMAN

Attesting Officer    Commissioner of Patents and Trademarks